United States Patent [19]

Giguere et al.

[11] 4,347,568

[45] Aug. 31, 1982

[54] OCCUPATIONAL HEALTH/ENVIRONMENTAL SURVEILLANCE

[75] Inventors: Edward L. Giguere, Parma; Paul H. Kaiser, North Olmsted; Gordon M. Campbell, North Ridgeville, all of Ohio; Peter F. Hoffman, O'Fallon, Ill.; Hansford Boutchyard, Jr., Brunswick, Ohio

[73] Assignee: Diamond Shamrock Corporation, Wilmington, Del.

[21] Appl. No.: 967,520

[22] Filed: Dec. 7, 1978

[51] Int. Cl.³ .............................................. G06F 7/00
[52] U.S. Cl. .................................... 364/300; 364/900
[58] Field of Search ............... 364/413, 415, 416, 417, 364/418, 300, 200 MS File, 900 MS File

[56] References Cited

U.S. PATENT DOCUMENTS

| | | | |
|---|---|---|---|
| 3,794,982 | 2/1974 | McCormick et al. | 364/900 |
| 3,872,448 | 3/1975 | Mitchell, Jr. | 364/200 |
| 3,970,996 | 7/1976 | Yasaka et al. | 364/900 |
| 4,053,951 | 10/1977 | Hudspeth et al. | 364/900 X |
| 4,075,680 | 2/1978 | Calle et al. | 364/200 |
| 4,130,881 | 12/1978 | Haessler et al. | 364/900 |

Primary Examiner—Gareth D. Shaw
Assistant Examiner—Thomas M. Heckler
Attorney, Agent, or Firm—Fay & Sharpe

[57] ABSTRACT

A method and computer system manipulates data concerning the health of a plurality of employees, each of the employees working in at least one work location and being identifiable by an employee identification, each of the work locations being identifiable by a work location identification, substances of which at least some are potential hazardous being or having been present in at least one of the work locations, each of the substances being identifiable by a substance identification. The computer system has an updated location data base which stores location identifications and is updatable to store additional location identifications, an updatable employee identification data base which stores employee identifications, an updatable employee health data base for storing employee health data concerning each of the identified employees, and an updatable substance data base which stores substance identifications. The data is stored in the interrelated data bases such that it is relatively easy to retrieve data concerning a specific employee, a specific substance, a specific work location, a specific employee health condition, or combinations of them.

26 Claims, 7 Drawing Figures

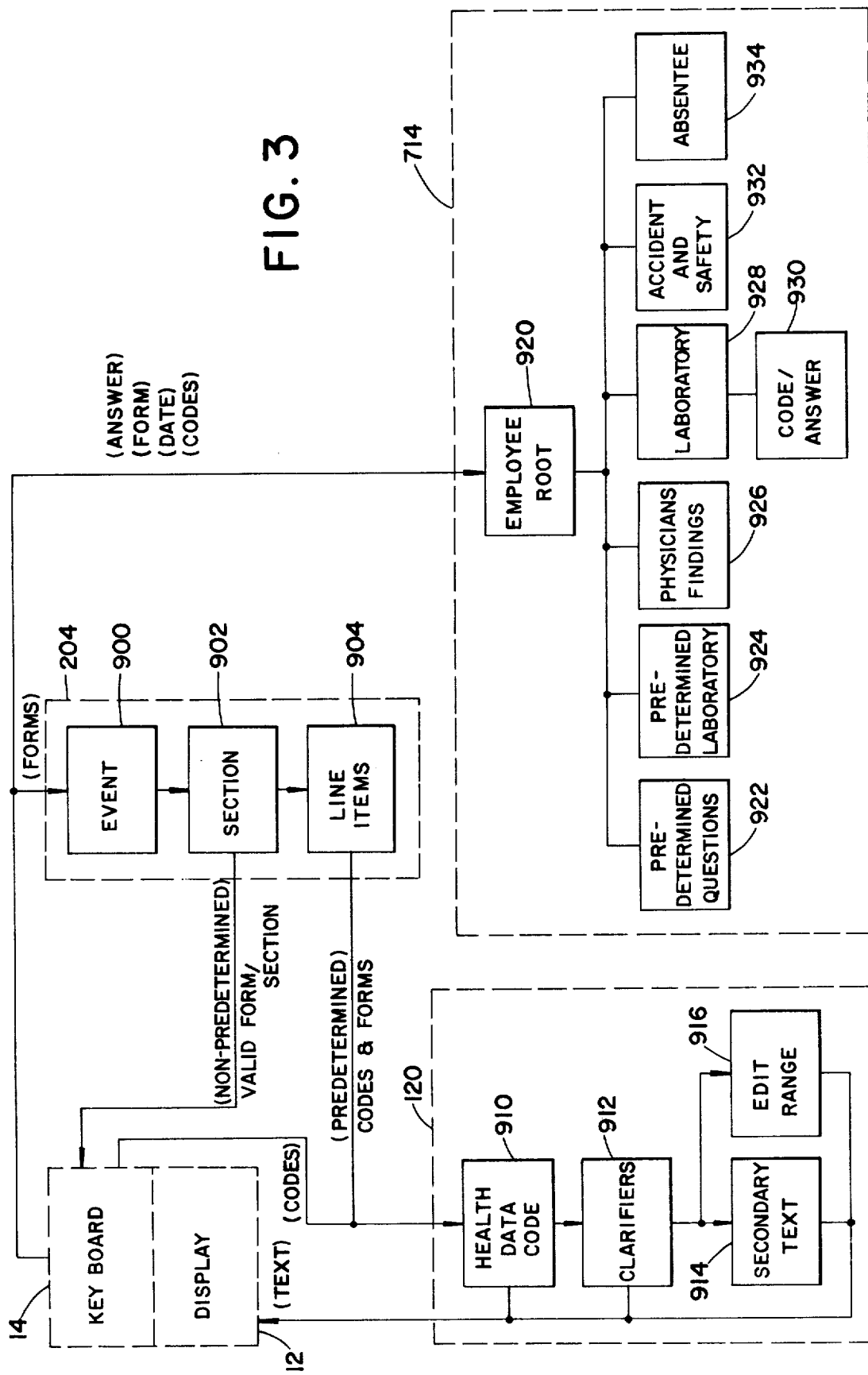

OCCUPATIONAL HEALTH/ENVIRONMENTAL SURVEILLANCE

BACKGROUND OF THE INVENTION

This application pertains to the art of monitoring environmental, accident and health factors within a work environment and more particularly reporting and pinpointing hazards in the work environment to allow for prompt, corrective actions.

The invention is particularly applicable to monitoring the health and environmental factors in chemical processing and manufacturing plants and will be described with particular reference thereto although it will be appreciated that the invention has broader applications such as the monitoring of the environment for health, accident and other defects in a variety of industrial, institutional and other situations.

Prior monitoring systems are commonly of a design to monitor recognized or suspected health and environmental problems. The simpler systems are cumulative recording devices such as a pen recorder for recording the amount of a hazardous particulate in the air, or a log book for manually listing potentially hazardous events on a periodic or event-keyed basis.

Annual physical examinations are commonplace. However, the results of the examinations are normally only correlated with currently suspected problems. The recognition of a previously unrecognized correlation between a medical diagnosis and a recognized problem produces an awkward dilemma. Previous physical examinations may include highly probative information but the task of re-evaluating and analyzing numerous medical records is an arduous time comsuming task. Further, annual or special physical examinations are keyed to the recognition of present and potential health hazards from medical diagnosis.

Corporations with a plurality of plants often have employees in several plants working in the same or related environment, contacting one or more of the same hazardous substances. Further, these employees frequently change jobs and change the substances with which they are working. In the past the health hazards from these hazardous substances were frequently monitored on a piecemeal basis because of the difficulty of correlating the health of past and present employees at a plurality of physical facilities.

Further, various government agencies such as the Occupational Health and Safety Administration (OHSA) and others require that health records be maintained on employees who have had contact with various toxic substances and that various reports and tabulations of these health studies be reported to the government. Other agencies such as the Environmental Protection Agency require other reports on the use of other hazardous substances. As new substances are recognized to be toxic or potentially hazardous these reporting requirements are changed. These changes cause many of the prior health reporting systems to be totally revamped in order to monitor different employees, to perform different medical examinations, and report different statistics to the government.

Further, prior health monitoring was primarily responsive to health or environmental problems. These systems are lacking in the ability to recognize correlations between problems an substances in the work environments. Generally, a severe problem occurs before the causes are determined an corrective measures unertaken.

SUMMARY OF THE INVENTION

The present invention contemplates a new and improved health and environmental monitoring system which overcomes all of the above referred problems and others and provides the basic tools for early detection of health and environmental threats in the work environment. In accordance with the present invention, there is provided a health and environmental monitoring system which monitors not only current health and health threatening problems but also maintains historical data which is easily reached and reorganized for discovering heretofore unrecognized health problems. It enables early recognition of health threatening situations so that remedial measures may be undertaken before severe problems occur. In accordance with a more limited aspect of the invention, there is provided a health maintenance system which is easily adapted to change the format and context of reports to meet the continuing changes in governmental, corporate and other reporting requirements.

In accordance with a more limited aspect of the invention, there is provided a health maintenance system in which the historic data is maintained on the basis of substances, chemicals and materials including those not specifically recognized to be hazardous, on the basis of medical conditions including the results of medical diagnosis not presently recognized to be abnormal, on the basis of physical location of employee work areas even those areas which are not presently recognized as having a health or safety threatening environment, and on the basis of employees including those employees not presently recognized as being within a health threatening environment or handling health threatening materials.

A principal object of the invention is the surveillance of the health status of employee populations in relation to their work environment in order to detect the most subtle changes at the earliest possible moment.

Another object of the invention is to enable research into early recognition of cause and effect relationships in the health status of employees and the work environment. In particular, the system enables correlation of medical defects with exposure to individual chemicals or materials or with exposure to combinations of chemicals or materials. For example, synergistic health threatening combinations such as cigarette smoking and exposure to certain chemical substances, e.g. asbestos, in which exposure to the combination is many times more hazardous than to either individually.

Another object of the present invention is to establish employee health norms, perform epidemiological studies, and make biostatistical evaluations. These enable early detection of health threatening factors within the work environment and allow for comprehensive treatment of employees previously subject to work and environment conditions which are newly recognized to be detrimental to health.

A further object of the invention is to enable easy modification of reporting format and content. This simplifies and quickens changes needed not to meet changing government requirements.

A still further object of the invention is to provide a convenient system for determining the employees who are due for medical examinations.

BRIEF DESCRIPTION OF THE DRAWINGS

Invention may take physical form in certain parts and arrangement of parts at the preferred embodiment of which will be described in detail in the specification and illustrated in the accompanying drawings which form a part thereof.

FIG. 3 is illustrative of data flow during key board operator medical data entry;

DESCRIPTION OF THE PREFERRED EMBODIMENT

Figure 1A:
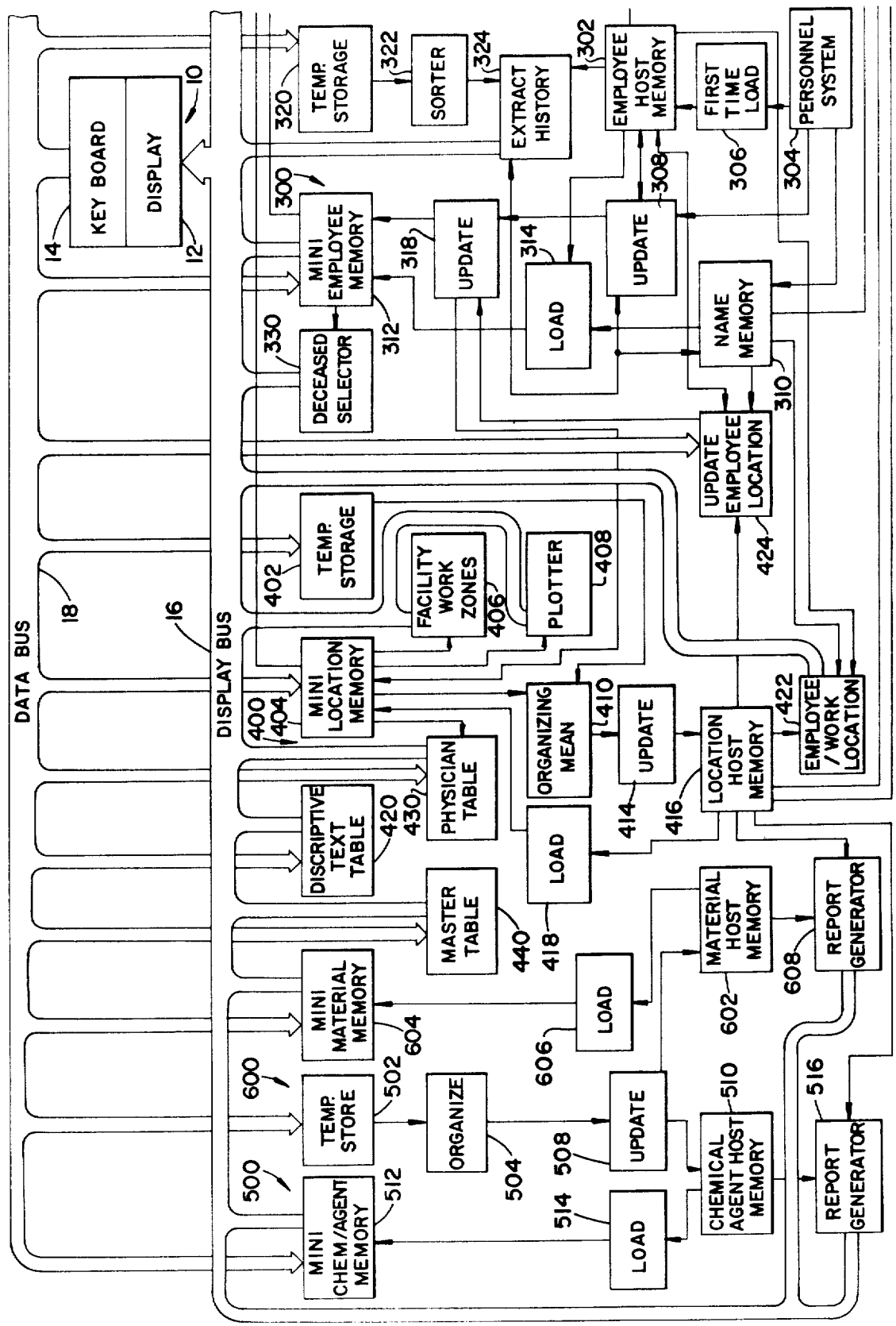
FIGS. 1A and B are a block diagram of a health and environmental surveillance system in accordance with the present invention.

Referring now to the drawings wherein the showings are for the purposes of illustrating the preferred embodiment of the invention only and not for the purposes of limiting it.

Figure 1B:
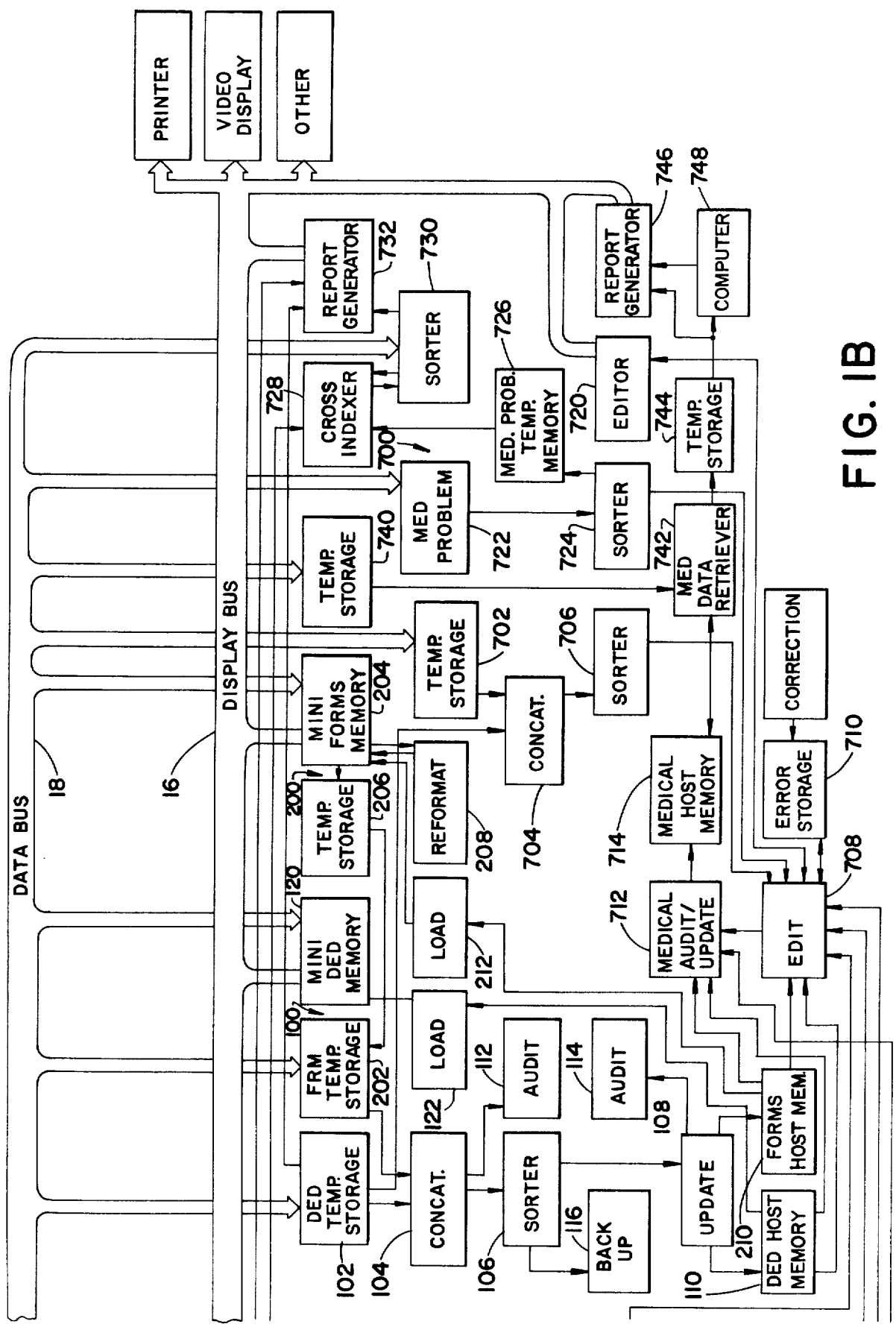

The block diagram showing an overview of the Occupational Health and Environmental Surveillance system is illustrated in FIG. 1. The overview is concerned with modifying the format and content of the data received. These modifications are manifested in the Forms used to report the data, the tests used to determine medical information to be recorded, changes in work locations, employees, chemicals, materials and the like. Specific stored Medical Information, Locations, Employee, Chemical and Material data may be drawn upon in various combinations an permutations for enumerable purposes.

The system includes a terminal 10 which includes a CRT or video display screen 12 and a data input means 14 such as a keyboard. Terminal 10 provides one mode of display for data stored in the system although other forms such as printers, reel tape or graphical plotters may be used. Similarly, keyboard 14 provides only one of many means of data entry for entering data to change the format, content, etc. of the information processed or entering medical information. Although only a single terminal 10 is shown, in most operations a plurality of such terminals are used. Connected with terminal 10 is display bus 16 for conveying selected information to the screen and other output displays. Also connected to the terminal 10 is a data bus 18 for conveying input data to selected parts of the system.

For simplified conceptual comprehension of the system, the system will be explained in seven subparts, however, the large amount of interfacing between various subparts of the system will become clear on viewing the system as a whole. The seven subparts of the system are a Data Element Dictionary means 100, a Forms sybsystem means 200, an Employee Index means 300, a working Location system means 400, a Chemical and Agent system means 500 and a Materials system means 600 and a Medical Information means 700.

In monitoring the health of employees there are many types of health data to be monitored such as injuries, sicknesses, safety, accidents and medical infirmaties. Further, the modes of monitoring include lab tests, doctor's prescriptions, treatments, diagnosis, symptoms, operations, routine physicals and nonroutine medical examinations. As medical science progresses new laboratory procedures an examination procedures are developed. These in turn expand the number of forms Medical Information may take. Further, progress of medical research, changes in government reporting requirements, cause more and different environmental conditions, health maladies, or injuries to be monitored. In addition to the need to receive new and different information, the same medical information can be received redundantly from a variety of tests, examinations and procedures.

The Data Element Dictionary means 100 includes an index to acceptable medical codes. These medical codes can be adjusted and modified to receive health, accident and other data in new forms or concerning new health and accident problems. When changes in the Data Element Dictionary vocabulary are to be made, an operator inserts the changes on terminal 10. The changes are conveyed by data bus 18 to the Data Element Dictionary means 100 where they are received by temporary storage means 102. When all the changes to the codes have been received and stored in the temporary storage means 102, they are organized by an organizing means such as a concatenation means 104 which organizes and coordinates the temporarily stored data and a sorter 106 which sorts the concatenated data. The organized data is conveyed to an updating means 108 for updating a host memory means 110. Various auditing and backup storages may be employed. For example, the concatenation means 104 and updating means 108 may each cause a written report of the new data or number of new data entries to be printed out from audit means 112 and 114 respectively. These paper reports may then be manually compared to guard against electronically induced errors or lost data. Numerous other audit control reports for comparing the data at different stages in its processing can, of course, be used throughout the system.

Another failsafe means which may be included at numerous points throughout the system is a backup means such as backup storage 116. This backup means temporarily stores the data which has been sorted by sorter 106 and puts it into storage either in a magnetic memory, or tape. Then if the system fails, the changes need not be re-entered individually again on terminal 10. Rather, the stored data in the backup means is returned directly into sort means 106. The more temporary backup storage means that are employed throughout the system the lower the chances become of loosing manhours re-entering data due to a system malfunction or of loosing the data. Correspondingly, however, the larger the number of backup storages, the greater the equipment costs and daily manhour requirements in manipulating the various backup means.

As changes in the health data codes become required, new codes are added and obsolete codes deactivated. The deactivated codes are retained to form an historical record of prior codes. The historical record serves to block further entry of data under deactivated codes, to enable retrieval of historical data, etc. Currently and historically used health data codes are stored in the host Data Element Dictionary memory means 110, as well as, a Mini-Data Element Dictionary memory means 120. The Mini-Data Element Dictionary memory means may be embodied as the memory of a mini-computer. Mini-Data Element Dictionary memory means 120 is connected with the display bus 16 to enable its contents to be displayed in whole or in part. This display may take the form of the accompanying text for guidance in interpreting or entering information or a printed dictionary of all available health data codes, etc. For example, when an encoded health code is typed into keyboard 14 Mini-Data Element Dictionary memory means 120 may be called upon to provide textural explanation of the code for display therewith on screen 12.

The Mini-Data Element Dictionary memory means 120 is connected with the data bus 18 so that it may be commanded to display textural explanations discussed above. Further, the data bus connection is used to update the contents of Mini-Data Element Dictionary memory means 120 directly without the circuitous route via host Data Element Dictionary memory means 110.

Examples of changes in the health data codes include the addition of new health data codes, changing the ranges of health data problems which are considered normal; deactivating health data codes from active use, adding ranges for normal or problem conditions to existing health data codes, etc.

Changes in the codes contained in Mini-Data Element Dictionary memory means 120 are made directly from terminal 10 at the same time the changes are conveyed to temporary storage 102. However, for first time loading or for recreating the data stored in Mini-Data Element Dictionary memory means 120 after a system failure or some other cause of the data becoming different in memory means 110 and 120, a loading means 122 is provided. Load means 122 adapts the current information stored in host Data Element Dictionary memory means 110 to the proper format and order to transfer it into the Mini-Data Element Dictionary memory means 120.

The Forms means 200 organizes medical data for storage. It determines memory addresses in the medical information means 700 for each health data code. Only the results of medical encounters are stored, the questions are not. The Forms means determines locations within the memory of the medical information means at which events or medical encounters corresponding to each Data Element Dictionary code are recorded. Events are employee-medical, interactions and may have subparts or Sections pertaining to specific medical examinations or tests. For example, Events include health examinations, annual examinations, pre-employment examinations, special examinations, clinic visits, health insurance claims, workmen's compensation claims, death certificates, random personnel samplings, and monitoring of specific work areas. The subparts or Sections of a medical event include types of diagnostic examination such as chest X-rays, blood pressure readings, electrocardiographs and so forth.

Various Forms are used for recording medical encounters. These Forms include predetermined questions requiring only a yes or no answer, predetermined questions with multiple choice answers several of which may be selected, predetermined questions for which the answer is a range of values, nonpredetermined questions, questions which are open-ended and information which is determined from other sources or questions. Examples of these questions may include in a pre-employment questionnaire "have you ever had epilepsy", or "which of the following diseases have you had . . . ", or in a routine physical "in which of the following ranges is the patient's white blood cell count", or "what does the chest X-ray show" or in a clinic visit, "what is the nature of the malady complained of." Open-ended and nonpredetermined questions may encompass information which is also covered by specific questions. Further, the various types of medical encounters listed above each use different forms on which the physician records his findings. These various Forms may request the same information with a variety of questions and question formats, e.g. multiple choice in one, yes/no answer in another, or a range in yet another.

Changes in the Forms are entered, for example, on the keyboard 14 of the terminal 10. Changes are conveyed directly to a Forms temporary storage means 202 until all changes have been entered. Additionally, the changes are conveyed to a Mini-Forms memory means 204. This Mini-Forms memory means, analogous to the Mini-Data Element Dictionary memory means 120, in the preferred embodiment is a minicomputer memory. To revise an existing questionnaire by command from keyboard 14 changed and unchanged parts of the questionnaire are conveyed from the Mini-Forms memory means 204 to a temporary storage means 206 for creating questionnaires. When the questionnaire is revised to the operator's satisfaction it is conveyed from temporary storage means 206 to temporary storage 202. The information stored in Mini-Forms storage means 204 is cycled through a reformat loop 208 which restructures the storage means 204.

Temporary storage means 202 is connected with concatenation means 104 which concatenates the Forms revisions as well as the Data Element Dictionary entries and conveys concatenated data to sorting means 106. Sorting means 106 sorts the Forms data and conveys it to updating means 108. The updating means adds the revised Form to a host Forms memory means 210. Memory means 210 analogous to host Data Element Dictionary memory means 110 stores the organizational relationships between current and historical Forms and stored Medical Information. Should Mini-Forms memory means 204 and host memory means 210 for some reason become unsynchronized concerning the Forms, a loading means 212 is employed to reload Mini-Forms memory means 204 from host memory means 210.

Mini-Forms memory means 204 is connected with the display bus to produce various outputs displays upon command from the data bus 18. Such displays may include printing of a single Form on a printer or a video screen, printing a dictionary of all available Forms on a printer, or the printing of text on screen 12 corresponding with encoded data to provide textual significance for an operator addressing various forms and questions, on keyboard 14.

Employee Index means 300 maintains an index of employees including employee identifications, names, addresses, work information and demographic information. The employee identification can be an employee's name, an employee number, or social security number. To maintain employee medical information in secrecy, the preferred embodiment uses social security numbers as an encoded identification. Further, many of the reports which the system may be used to generate report statistical evaluations, numbers of employees with a certain medical problem, numbers in contact with a certain chemical, etc. Frequently, the identity of any one of the employees in a report is not significant. Occasionally, however, it is necessary to identify employees specifically. For example, when a correlation is discovered between contact with a specific chemical and a pecific malady or a correlation between exposure to a pecific combination of chemicals and a specific malady, it is desirable to be able to identify all employees who have been so exposed in order that they may be given special medical examinations and treatment.

Unlike the Forms and the Data Element Dictionary, changes in Employee Identification are not regular occurrences. Rather, the changes are generally limited to the acquisition of new employees and employee's terminations by retirement, severance or death. The severance of employees from the corporation does not dispose of their employee identification rather it is retained for use in conjunction with the historical medical information.

Information concerning changes in the employee staffing are commonly handled by a personnel department. In the preferred embodiment, the personnel department continues to maintain the employee's records and the present system interfaces with a personnel computer program to ascertain changes in employee staffing. A host Employee memory means 302 is interfaced with a personnel system 304 to receive new employee data directly. To create an initial Employee Index, a first time load means 306 is provided for loading the host Employee memory means 302 when the system is first put into operation. Thereafter, changes and updates to the personnel system are conveyed to an update means 308 for updating the host Employee memory means 302.

To maintain employee privacy, host Employee memory means 302 does not store the employee's name but only identification number. To make the employee's name available in selected situations, a name and address file is stored in a Name memory means 310. By addressing memory 310 with an identification number, Name memory means 310 is caused to generate the name and address of the corresponding employee.

Again host Employee memory means 302 stores data on past and present employees. A Mini-Employee memory means 312, such as a minicomputer memory, maintains a file of employees including their names. To create the Mini-Employee Index a load means 314 conveys employee information from host Employee memory 302 and names and addresses from Name memory 310. Thereafter, employee changes are conveyed via update means 308 to an employee memory update means 318 for updating the Employee memory means 312. Similarly, the new names are conveyed from name memory 310 via update means 308 and 310. The changes are transformed in employee memory update means 318 to match the format of Mini-Employee memory 312.

When an operator at terminal 10 desires employee information, he may either address Mini-Employee memory means 312 for obtaining name, current address and current work location or host Employee memory means 302 to obtain historical data including age, sex, date hired, prior work locations and dates worked. Historical employee information requests are conveyed from terminal 10 on the data bus 18 to a temporary storage means 320. The temporarily stored request is sorted in a sorter by 322 and read by a history extraction means 324. The history extractor addresses the host Employee memory means 302 and ascertains the requested information. Requested information is conveyed from the host Employee memory means 302 through the history extraction means 324 to display bus 16.

Mini-Employee memory 312 is also interconnected with the data bus 18 and display bus 16 so that selected information can be obtained from that memory. One specific readout from Mini-Employee memory 312 is the deceased employee report. A means 330 is connected with the current memory for monitoring the updates and selecting all employee status updates in which the update code indicates that the employee is now deceased. The deceased employees selection means 330 is connected with the display bus 16 so that a periodic report may be generated listing those employees who have recently become deceased. An analysis of these reports on a statistical basis may be helpful in recognizing heretofore undetermined causes of acute medical problems.

Closely related to the Employee Index means 300 is Location Identification means 400. Work locations provide a link between the employees who work in them and the potentially hazardous substances which are found at various locations. Work locations are specific as to facilities or plant locations, to areas within a plant location, and zones within each area. A zone is generally the smallest region in which all employees are prone to be subject to the same conditions or environmental factors. Within a given plant there is generally some floor area containing a plurality of different production functions for example, one of these zones may be used for batch processing of chemicals. This zone may, for example, be a relatively compact region surrounding a single chemical reaction chamber.

An area is composed of several zones. For example, several zones for batch processing chemical products may be located adjacent to each other in a single facility. Some employees such as foremen and maintenance employees split their working hours among several zones and are subject to factors occuring in each zone. Further, noise polution, chemical fumes and other factors affect an area including several zones.

There are two major types of location updates which the system performs. The first is the changing of work zones in which an employee works when the employee is moved or transferred from one job site to another or has his duties changed. Normally, a monthly report is made indicating the work zone or zones of each employee or at least those employees which have changed their work zone or zones in whole or in part. The second type of update occurs on an irregular basis when the use to which specific square footage of a facility is changed. For example, adding new lines, expanding old lines or discontinuing old lines. These employee location and work zone boundary changes are generated in terminal 10 and conveyed by data bus 18 to a temporary storage means 402 and to a Mini-Location memory means 404 such as a minicomputer memory. Temporary storage means 402 collects all the changes for concatenation and loading into a host Location memory at one time. Mini-Location memory means 404 maintains a file of all location codes. Interconnected with Mini-Location memory 404 is a means 406 for extracting from memory 404 an index list on a facility by facility or other basis of all the work zones currently in use. This means is interconnected with display bus 16 for printing a directory or displaying accompanying text on video screen 12, etc. Also connected to Mini-Location memory means 404 is a means 408 for creating graphical plots. This means such as a multipoint plotter is connected by display bus 16 to a graphic display type printer or a video screen to create a pictorial display showing the floor plan of a selected facility with demarcations showing the different work zones. To produce such a plot, the zones are defined in terms of an x, y and z coordinate system. To update a host Location memory a data organizing means 410 is interconnected with Mini-Location memory means 404 and temporary storage 402 for concantenating and sorting the data. An update means 414 receives the concatenated and sorted data for updating a host Location memory means 416. The host Location memory means 416 maintains a record of current and historical location data.

To provide the corresponding textual descriptions to accompany encoded messages, a descriptive text table 420 is provided. Mini-Location memory means 404 is reloaded whenever the stored Mini-Location data in Mini-Location memory means 404 becomes out of synchronization with the data in host Location memory means 416. Table 420 is connected with the data bus 18 and display bus 16 for the purpose of supplying corresponding text labels to accompany location descriptive information appearing on the screen 12.

Also interconnected with host Location memory means 416 is a means 422 for generating an employee work location report. Periodically, this means draws upon host Location memory means 416, Name memory means 310 and the host Employee memory means 302 to generate an output on the display bus for generating a directory of employee work locations. This directory is suitable for use in updating or noting the changes in employee location. It can be circulated to various employees or supervisors for correction of out-of-date employee work location information.

The Location, Employee, and Name host memories also interface for updating Mini-Employee memory means 312. An updating means 424 draws upon host Location memory means 416, Name memory means 310 and host Employee memory means 302 to ascertain information on employees and work locations. Information regarding changes is loaded into update program 318 for updating Mini-Employee memory 312 and Mini-Location memory 404. Changes in employee location can be read onto data bus 18 from a card reader or the like, and information supplied through a sort means to update means 424.

In addition to monitoring employee locations, generally, the system monitors the location of medical personnel separately. A medical personnel storage means 430 stores information on the medical personnel and their current locations. Storage means 430 is connected with Mini-Location memory for updating therewith. Medical personnel storage means 430 is addressable with data bus 18 to convey to display bus 16 information regarding a specific medical personnel by location of medical personnel or location or a directory of all medical personnel and their location.

A master label storage means 440 which stores a table of all the job code labels, status code labels and other labels and definitions is interconnected with the display bus 16. It provides textual support of the various codes appearing in various displays.

A Potentially Hazardous Substance means monitors mixtures, chemicals, materials and agents in the work environment. Potentially Hazardous Substances include purchased substances, saleable products and intermediate reaction products which are currently believed to be hazardous or which in the future may be believed to be hazardous. The Potentially Hazardous Substance means includes a Chemical and Agent means 500 and a Material means 600 for monitoring the potentially hazardous substances in the work environment. Chemicals generally include pure chemical substances such as those that form starting materials. Agents include other potentially dangerous physical factors or environmental conditions such as noise, dust, heat, etc. Materials are usually more than one chemical and include intermediate reaction products and final products of a production line. A material, however, may also be a chemical, e.g. a final product such as chlorine is also a pure chemical substance.

The Chemical/Agent subsystem identifies chemicals with the Chemical Abstract Society Numbers which are the common identifications used by scientists, engineers and research personnel. The Data Element Dictionary on the otherhand is based upon the International Classification of Diseases Abstracted, hospital version (H-ICDA) notation for identifying Chemical/Agents. The H-ICDA notation which is the common system used by hospitals and medical professionals, is less exacting then desired. Accordingly, the health data codes expand upon the H-ICDA notation to define maladies, diseases, laboratory tests and analyses more specifically, and to define medications.

Modifications in the Chemical and Agent system 500 are conveyed on the data bus 18 from terminal 10 and are received by a temporary storage means 502. After all of the chemical and agent modifications have been received in temporary storage means 502 they are concatenated and sorted by a data organizing means 504 and supplied to an update means 508. Update means 508 updates a host Chemical and Agent memory 510. Host Chemical and Agent memory means 510 stores all chemical and agent data both current and historical. A Mini-Chemical and Agent storage means 512 which stores chemical and agent data is connected to data bus line 18 to receive the same modification as temporary storage means 502. Mini-Chemical and Agent memory means 512 is loaded directly from host Chemical and Agent memory means 510 with a load means 514 which initially loads memory means 512 or reloads it when the information in memories 510 and 512 become out of synchronization. Mini-Chemical and Agent memory 512 is connected with display bus 16 to supply accompanying text to displays and for producing reports.

A report generator 516 is connected with host Chemical and Agent memory means 510 and host Location memory 416. The report generator can be actuated to generate any one or more of several reports which draw upon current and historical Chemical, Agent and Location information. Such reports may include an alphabetical listing of chemicals and agents or a tabular listing of chemicals and agents by location, etc. The output of the report generator 516 is again connected to display bus 16 for connection to display devices.

The Material means 600 partially overlaps with the Chemical and Agent means. Changes in Material data generated on data bus 18 are again received by temporary storage means 502, concatenated and sorted by data organizing means 504 and relayed to updating means 508. Updating means 508, however, with regard to material updates host Material memory means 602. Further, the material means includes a Mini-Material memory means 604. Mini-Material Memory means 604 receives material data changes directly from data bus 18 to maintain the stored material data. Initially or if memories 602 and 604 becomes out of synchronization, Mini-Material memory 604 is loaded directly from the host Material memory 602 by a loading means 606. Mini-Material memory 604 is connected with display bus 16 to supply accompanying text to displays and for producing reports.

A report generation means 608 is connected with the host Material memory 602 and with host Location memory 416. The report generator can be actuated to generate numerous reports which may draw upon current and historical Material and Location information. Such reports may include alphabetical listings of materials, tabular listings of materials by location, etc. The report generator means is connected with display bus 16 for connection with report printing or other display devices.

The Data Element Dictionary, Forms system, Employee Index, Location Identification, Chemical and Agent, and Material subsystems maintain the Occupational Health and Environmental Survelliance System in an up-to-date form to accept medical data and to generate reports based on new and historical data. Medical Data means 700 is a means for receiving Medical Data for storage. Interconnected with the Medical Data means may be any number of different apparatus for extracting the data to generate any type of report desired. In addition to generating reports, the system may be interconnected with a programmable computer for searching the stored data to find correlations and interrelationships thereamong which are statistically significant. Such retrievals may perform valuable medical research by searching the medical history files to determine links between various maladies and one or a combination of chemical, agent, environmental material or location factors. Sophisticated retrievals may determine synergistic effects among two or more causes in producing a malady which neither alone causes. The invention herein enables the generation of a seemingly endless variety of reports and uses. Details of these uses and reports are not a part of the invention herein.

Medical, Accident and Safety information is transmitted via the data bus 18 to a temporary storage means 702. This medical data includes lab results, physician findings, the answers to questionnaires completed by physicians or by employees, etc. Accident and Safety information includes details of accident, e.g. the nature of the injury, the cause of the accident, the agent which caused the accident, etc. Accident and Safety information is useful in determining where the safety standards are inadequate or inadequately enforced.

Medical, Accident and Safety temporarily stored in temporary storage means 702 is conveyed to a concatenation means 704. Concatenation means 704 is interconnected with Mini-Data Element Dictionary means 120 to assure the entry of new medical data codes before similarly coded medical data. The concatenated data is sorted by a sorting means 706 and conveyed to an editing means 708. Editing means 708 compares all the data received from sorting means 706 to determine whether it is true data. That is, it checks the reported employee identification against known employee identifications in host Employee memory means 302; checks the health data codes against those stored in the host Data Element Dictionary memory means 110; checks codes indicative of forms against host Forms memory means 210; and checks reported locations identifications against the valid location codes from host Location memory means 416. Any data which does not match the encodings in these memories is transferred to an error storage means 710 such as a tape drive means until corrected. Correction may be achieved by merely re-editing the data in error storage 710 to correct encoding errors. Occasionally new codes will be used with Medical, Accident and Safety data before they are defined in the appropriate part of the system. Reintroduction of the data in error storage 710 will cure errors caused by tardy entry of new definitions. Manual correction of errors in error storage 710 may be used. For example, if storage 710 is punch card, the cards may be manually inspected and repunched as needed.

Proper medical, Accident and Safety data from editing means 708 are conveyed to a medical encounter audit and update means 712. The audit and update means 712 is interconnected with the host Data Element Dictionary memory means 110, the host Forms memory means 210 and host Location memory means 416. Audit and update means 712 updates a main Medical memory means 714 which incorporates the new data into the medical history.

Newly entered Medical, Accident and Safety data is also conveyed to a second editing means 720 which extracts preselected types of data from the editing means 708. The extracted data is conveyed via display bus 16 to printers or video terminals to display summary reports.

A report is generated concerning certain flagged medical problems. The report may list newly entered flagged data only or newly entered flagged data and/or recent flagged data such as flagged medical problems occuring in the past month, the past six months, etc. To this end, newly entered medical data which has been flagged as a medical problem are channelled to medical problem temporary storage means 724. Edit means 708 similarly selects previously entered flagged medical problems. The newly and previously entered flagged medical problems from memory 722 and edit means 708 are conveyed to a sorting means 724. The sorted flagged medical problems are stored in Mini-Master Medical Problem storage means 726. The stored medical problems are cross-indexed with employee identifications from Mini-Employee memory 312 by a cross-indexing means 728.

Under control from data bus 18 a sorter 730 selects flagged medical problems and corresponding employee identifications or flagged employees and their Medical, Accident and Safety data for conveying to a report generator 732. The control from data bus 18 may further select the time period limitations for such medical problems e.g. problems occurring in the past month, the past six months, the past year, the past several years, etc. Report generator 732 is also connected with the Mini-Data Element Dictionary memory means 120 and the Mini-Location memory means 404 to supply the appropriate text on printed and other displayed reports. A variety of reports may be generated such as the number of reoccurrences of the flagged problem, the number of new occurrences of the flagged problem, the number of new occurrences by facility, a directory of flagged problems, etc. To facilitate reviewing of reports by those interested in only a single medical problem or single work location or employee, an index may be generated referencing limited areas of reports.

Other reports can be derived from the host Medical memory means, from the combination of host memory means, or from edit means 708. To retrieve data to generate other selected reports, the keyboard is connected with a retrieval temporary storage means 740. A retrieval request from the temporary storage means is organized into the appropriate format for a medical data retrieval means 742 for searching and retrieving the requested data from at least the main Medical memory means 714. The retrieval means conveys the retrieved data to a temporary storage means 744. A report generator 746 reorganizes the data from temporary storage 744 to the format appropriate to the report. A computer means 748 may perform a statistical analysis or other manipulation of the data for the report generator. Report generator 746 is connected with the display bus for displaying the report on a CRT, printer or other display device.

The interaction of the host Data Element Dictionary memory 110, host Forms memory 210 and main Medical memory means 714, during medical data entry, has ramifications in the simplicity or complexity of data entry and retrieval. The specific encoding and data base organization, if a programmable computer is used, affects the amount of hardware and machine time required to operate the system. Before looking to the preferred data base organization of these three memories, reference will be made to the preferred embodiment of the method of encoding data.

Figure 2:
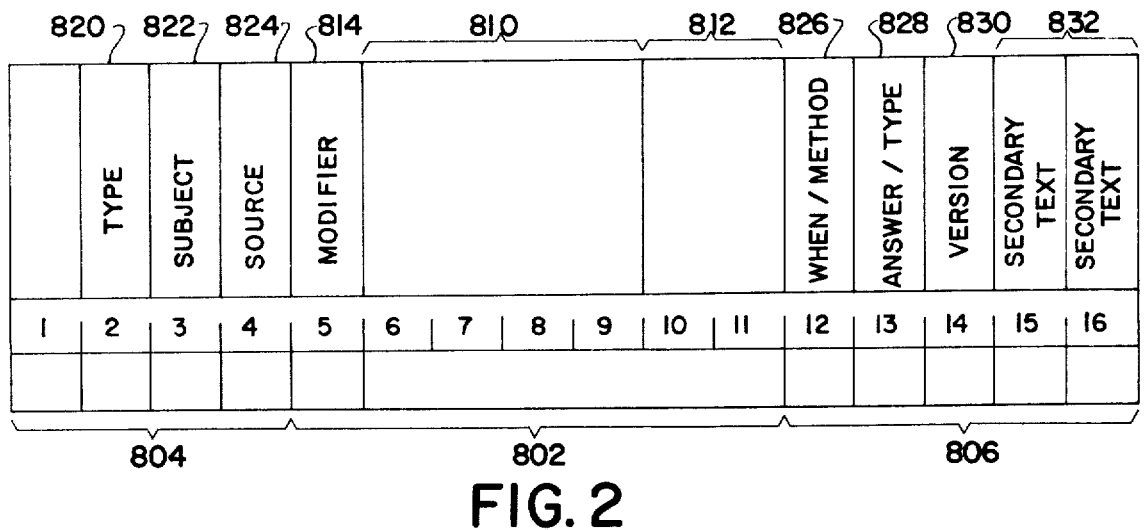
FIG. 2 is illustrative of a system of coding.

FIG. 2 is illustrative of the preferred encoding. The encodement is a 16 byte code, labeled a Health Data Code, which consists of a health code 802, prefix clarifiers 804 and suffix clarifiers 806. The health code 802 identifies medical conditions, maladies, treatments, medications, accidents, exposure to potentially toxic substances and the like. The basis of the health code is the four byte standard H-ICDA Code 810. In some instances the H-ICDA codes are not as specific as desired. To allow the H-ICDA code number to be further refined two additional bytes 812 are provided. This allows the health code to be divided into up to 100 subcategories. For example, the H-ICDA code provides a number for "smallpox (variola)". These two addition bytes allow this four byte code to be expanded to specify variola major, variola minor, etc.

Provision is made for a modifier 814 for modifying the meaning of an H-ICDA number for purposes beyond the normal uses or ranges of the H-ICDA code. The modifier indicates whether the four byte number 810 is used as an H-ICDA code, as a supplemental code for maladies and the like for which no provision is made in the H-ICDA, in another context of the H-ICDA code number, or other code numbers. For example, the H-ICDA code can be used with one modifier to indicate the existence of a medical condition, with another modifier to indicate treatment for the medical condition or with yet another modifier to indicate tests for or measurements of the medical condition, etc.

The clarifiers 804 and 806 supply who, what, when and where type information for providing the context in which the health code is used. The clarifier may include a type clarifier 820 for identifying the type of medical data. The types include questionnaire data, laboaratory data, physician's findings data, safety data and non-medical data.

Another clarifier is a subject clarifier 822 for identifying the person to whom the health code applies. This subject code shows whether the health code applies to the employee himself, his immediate family, his grandparents, and so forth. A history of the condition in an employee's family is helpful in determining the significance of medical conditions which are heredity linked.

Another clarifier is a source clarifier 824 for indicating the source of the medical data. The sources include employee diagnosed or identified conditions, conditions reported by the employee based on prior medical opinions, medical diagnoses by the reporting physician, conditions for which the employee was hospitalized, and conditions reported by the employee's supervisor. This indication reflects upon the accuracy and reliability of the data. The source of laboratory type data is an indicia of the laboratory test or equipment used to determine the data. These laboratory sources include EKG, audometry, perometry, whole blood, plasma, serum, urine, vision, X-ray and miscellaneous.

Other clarifiers are the when and method clarifiers 826. The when clarifier is for indicating the time in the past at which a condition is reported to have existed or a diagnosis reported to have been made. The when clarifier is used primarily with questionnaire data. Because laboratory tests generally test a present condition, when is not appropriate to laboratory tests. However, the same condition can often be diagnosed with any one of a number of laboratory test procedures. For laboratory tests a method clarifier is used for identifying the laboratory procedure with which the condition was diagnosed.

An answer clarifier 828 indicates the nature of the answer. Such clarifier states whether the answer is to be in the form of a quantity, frequency, yes/no, body part, pain discription, duration, relieved by, treated by, change in, etc. This clarifier shortens the answer, by allowing the answer to be merely a number, medication or the like. The clarifier supplies the significance of the number, medication or the like.

A version clarifier 830 identifies the lexacography of the questionnaire. Each time a question in a questionnaire is reworded, it is assigned a new version identification. Thus, if all versions are not fully synonymous, compensation for the variation can be made.

A secondary text clarifier 832 indicates that a textual answer is provided. The secondary text number may be in bytes 15 and 16 for multiple choice answers.

When encoding laboratory test data no answer or version clarifiers are required. Rather, bytes 828 and 830 form a two byte type of exam or test clarifier. This clarifier identifies such types of laboratory exams and tests as biological compound, cell count, culture, cytology, enzyme determination, hormone, ion determination, microscopic determination, protein determination, physical determination, toxic level determintion, violatile gas, immunological testing, and the like.

It may be noted that only 15 bytes of the 16-byte code are identified. Byte 1 is not currently used and may not be used to assist or specialize the system in the future.

FIG. 3 illustrates the data flow in the Mini-Data Element Dictionary Mini-memory 120, Mini-Forms memory 204, and main Medical memory 714, respectively. The flow of data in the preferred embodiment is, of course, keyed to the encoding illustrated in FIG. 2.

To enter medical data on keyboard 14, the Form of the Medical Data is first identified. This Form identification includes the Event, such as annual exam or pre-employment physical, and a Section, such as the employee questionnaire, chest X-ray, or other part of the Event. The Mini-Forms memory 204 has a record or means 900 for Events. Under each event for which provision has been made there is a record 902 for the Sections for which provision has been made. For each section which is designed to receive predetermined data, such as questionnaires, there is a further indented Line Item record 904. A questionnaire, as used herein, as a fixed set and order of questions. To save memory space and data entry time, the answers only of predetermined questions are stored. The Line Item record idenfies each predetermined question and coordinates the answer with their predetermined question. Additionlly, record 904 supplies a serial list of the health codes or each question on the selected questionnaire for use n producing a display to the operator entering data.

The Mini-Data Element Dictionary memory 120 eceives the serial list of health codes from record 904 f the Mini-Forms memory. In particular, record 910 of he Data Element Dictionary host memory receives the even bytes of the Health Data Code 802. Health code ecord 910 causes retrieval of the text corresponding to he Health Data Code for display on the CRT display. Record 912 receives the clarifiers and similarly causes etrieval of the text for the next question to be answered. If the questions are multiple choice, record 914 etrieves the text of the alternatives.

The employee identification number and the predetermined health codes from the Mini-Forms memory nd the corresponding medical data are received by the main Medical memory 714.

The main Medical memory 714 organizes the medical data first by employee at employee root record 920. Under each employee it provides several areas and ypes of storage. At predetermined questions storage record or means 922, it provides for storage of answers to predetermined questions. The stored predetermined question data of each entry consists of an identification of the Form followed by a continuous string of answers. To interpret the stored data, the host Forms memory for each identified form supplies each question and the segment of the continuous string of answers which is the corresponding answer. The text of the supplied questions is provided by the Data Element Dictionary memory. A storage means 924 for predetermined laboratory text results again stores the Form identification and a set of answers.

Nonpredetermined data is provided for slightly differently. In the Mini-Forms memory, nonpredetermined data is sorted by the Event identification at record 900 and the Section identification at record 902. Because the data is not predetermined, however, Line Item record 904 is unable to supply a predetermined sequence of corresponding Health Data Codes. Rather, the operator entering the data evaluates the nonpredetermined data and determines the appropriate Health Data Code. The code is then operator supplied, at least in part.

The Data Element Dictionary 120 receives the operator supplied health code from the keyboard at record 910. Record 910 causes the textual label for the seven byte Health Data Code 802 to be displayed on screen 12 for sight verification. Similarly, record 912 causes the retrieval of text corresponding to the clarifiers. For each clarifier set, an edit record 916 is provided. This provides the reasonable ranges for medical data of the encoded type. The reasonable range is used to identify clearly erroneous encoding of medical data. For example, an answer of 200 is reasonable for an employee's weight in pounds, but unreasonable for his height in inches. Accordingly, the edit range for a health code for weight would include 200, but a health code for height in inches would exclude 200.

Nonpredetermined data and the operator encoded health codes are received by the main Medical memory at record 920. The proper storage means for the answers and codes is determined from the clarifiers and the answers and codes channelled thereto. One such storage means is the physician's findings storage means 926. In storage means 926, the Forms, answer, data and seven byte health data code are stored. It is unneccessary to store the clarifiers because with the encoding method of FIG. 2, physician's findings all have essentially the same clarifiers.

Another storage area for nonpredetermined laboratory data is composed of storage means 928 and 930. A first means 928 stores the Form and the date. A second means 930 under each Form segment stores the health code and the answer.

Also in the medical memory are storage means 932 for accident and safety data and 934 for absenteeism. Accident and safety storage means 932 is set up essentially the same as storage means 926. All accident and safety codes having essentially the same clarifiers, only the Form, data, and seven byte Health Data Code need be recorded. The absentee storage segment records an indication of employee absences.

Figure 4:
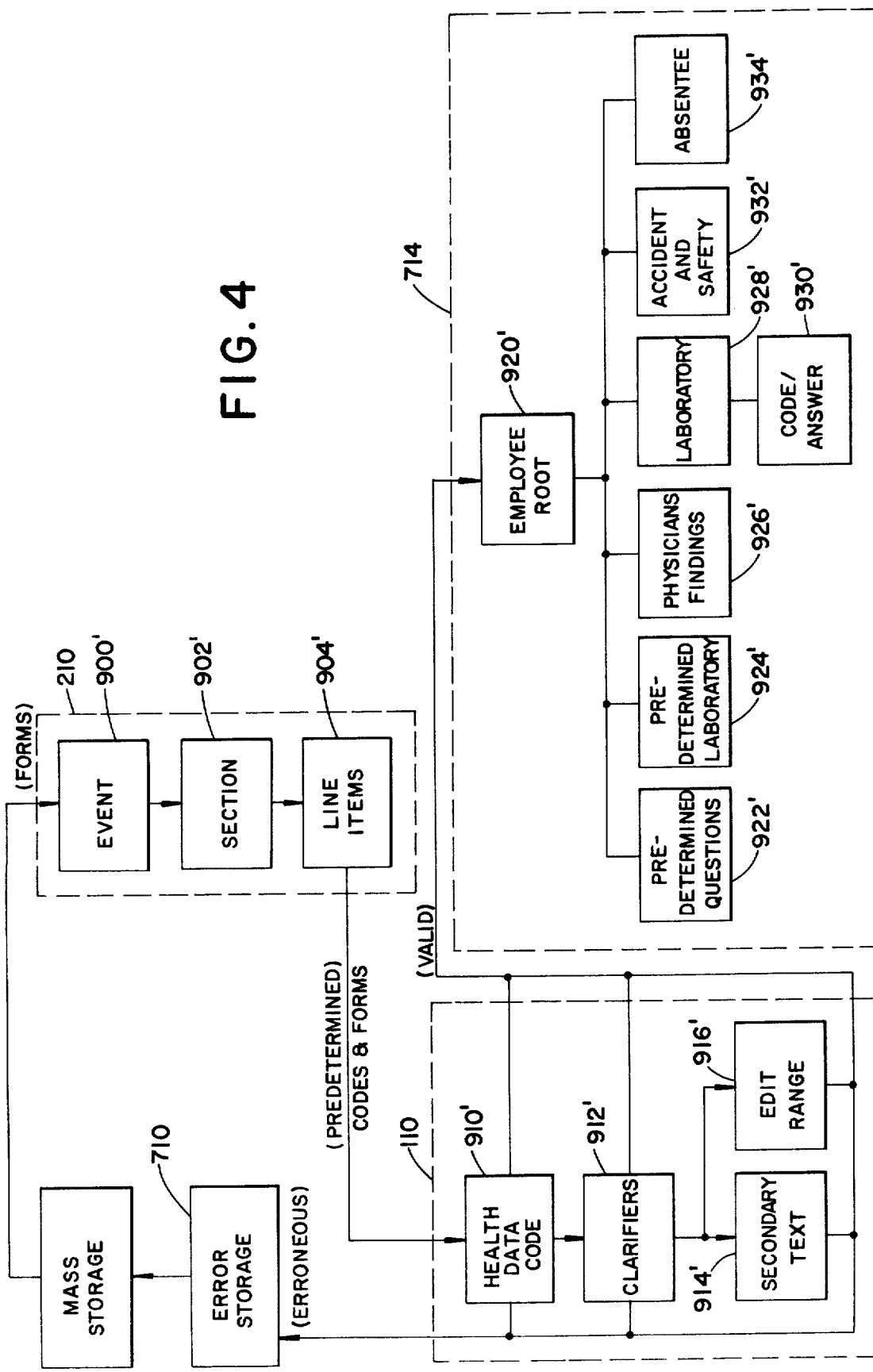
FIG. 4 is illustrative of data flow during mass storage medical data entry.

The flow of data entered from mass storage, such as tape, is illustrated in FIG. 4. Tape entered data is predetermined in the preferred embodiment. It will be appreciated that FIG. 4 is analogous to FIG. 3. To highlight the similarities analogous elements are marked with the same reference numeral followed by a prime ('). The Forms data is received by host Forms memory means 210 which supplies a serial list of health codes for each question of the identified questionnaire. The host Data Element Dictionary memory 110 receives employee identification, answers, dates, serial list of health codes and the like. Health code record 910' and clarifier record 912' identify not provided for or otherwise erroneous on their face health codes and clarifiers. Edit means 916' identifies answers which are not within the reasonable ranges for Medical Data of the encoded type. These identified errors are collected and stored in error storage means 710 for future manual correction. The data stored in error storage means 710 may be re-entered with new data entries. In this way errors which are caused by the entry of data, codes, clarifiers and the like for which no provision was made will be accepted as proper data after such provision is made.

Main Medical memory means 714 receives the valid employee identification number, date, Form identification, health codes, and answers from the Element mass storage device. To the main Medical memory, the received data is the same whether mass storage entered or keyboard entered. The data is again stored in the appropriate one of storage means 922-934.

Figure 5:
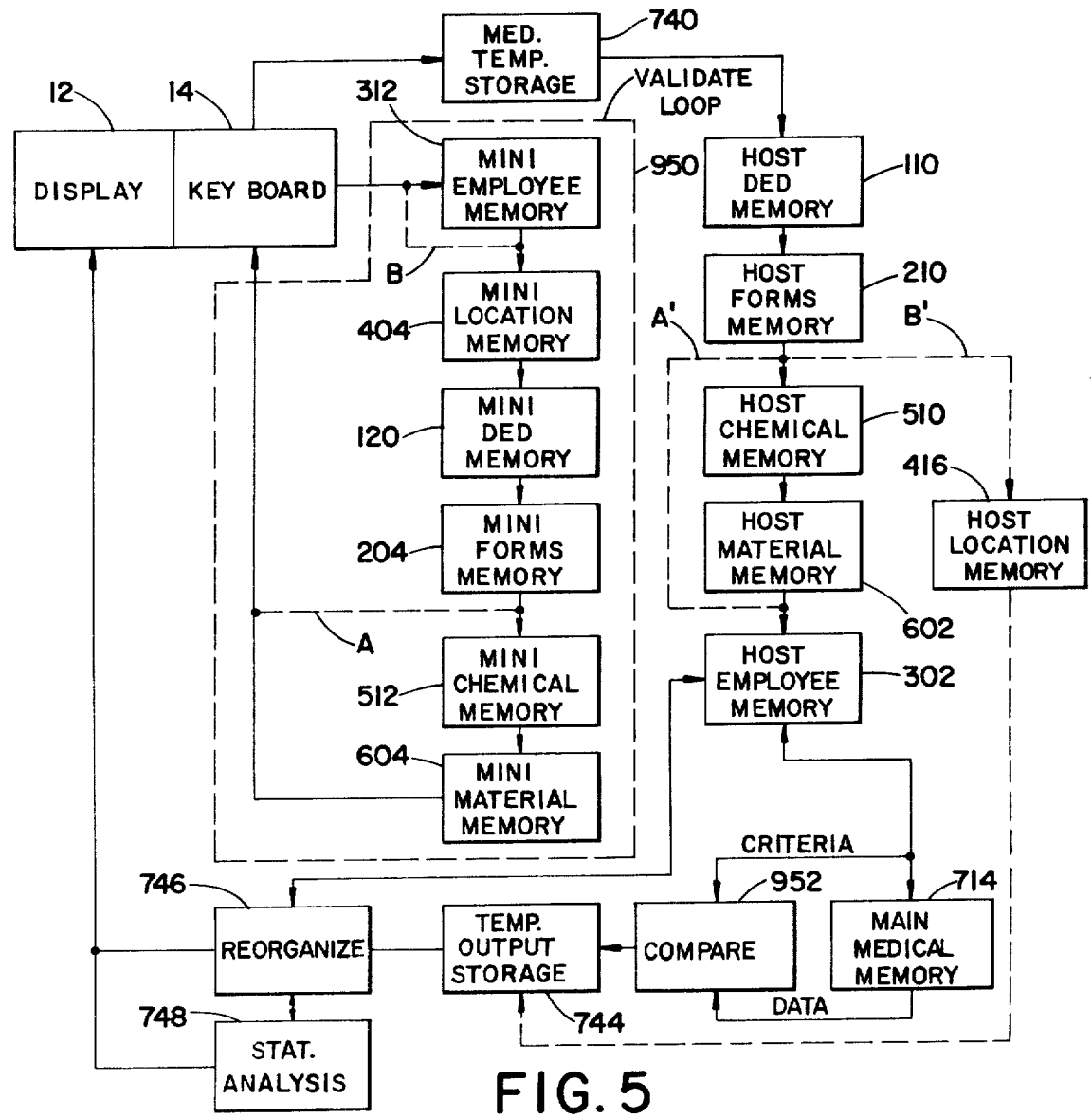
FIG. 5 is illustrative of data flow during medical data retrieval.

FIG. 5 is illustrative of flow paths for data retrieval. The nature of the data to be retrieved is encoded to form a data request. The retrieved data includes medical data, employee-potentially hazardous substance contact data, malady-potentially hazardous substance interrelationship data, workplace monitoring for potentially hazardous substances data and many others. The data request is entered by the operator at keyboard 14 or other data entry means.

The data request is processed through a validation loop 950. This loop compares each encoded part of the request with the permissable codes in the appropriate ones of the Mini-memory means. The request in the preferred embodiment is compared with the alotted employee identifications in Mini-Employee memory 312 and with the allocated location codes in Mini-Location memory 404. These comparisons insure that limitations in the request to specified facilities, employees or employee group will not call upon the host memories with codes they are not prepared to receive. Accuracy of the location code is further important because it interconnects the employees and the potentially hazardous substances.

Encoded parts of the data request are further compared with provided codes in Mini-Data Element Dictionary memory 120 and the Mini-Forms memory 204. These comparisons insure that the maladies and tests or for questions about maladies are in fact encoded in the host memories.

Additionally, the encoded request is compared with available chemical, agent and material codes in Mini-Chemical/Agent memory 512 and Mini-Material memory 604. These comparisons insure that potentially hazardous substances concerning which information is requested are substances about which data is stored.

For some types of data requests, it is unnecessary to compare the request with all Mini-memories. Requests which are not concerned with potentially hazardous substances, such as a request for employees with coronary disease who also smoke, may bypass the Mini-Chemical memory and the Mini-Material memory as illustrated in phantom by path A. Requests which are not keyed directly to specific employees in the employee population, such as a request for levels of a potentially hazardous substance detected in the workplace at automatic area monitoring stations, may bypass the Mini-Employee memory along path B.

If all the codes are valid, the request passes to temporary medical storage 740. To reduce computer time, it may be desirable to limit the number of health codes for each request. The request is channelled to the host Data Element Dictionary memory 110 for identification of the Health Data Code.

The host Forms memory 210 identifies the forms, locations within predetermined questionnaires, and other locations in which the identified health data code appears.

Host Chemical/Agent memory 510 and host Material memory 602 identify the work zones and areas and time periods in which a specified potentially hazardous substance was used.

The host Employee memory 302 determines which subpopulations of the employee population are to be sampled. This determination may be made in the request or derived from the work Location designated by memories 510 and 602, or in other manners as flows from the nature of the request.

If the request does not concern Potentially Hazardous Substances the host Chemical and Material memories can be bypassed as illustrated in phantom by path A'.

From the Employee Identifications, Form Identifications, and Health Data Codes the pertinent areas of storage means 922, 924, 926 930, 932 and 934 are selected. Further, the exact storage locations in predetermined data storage means 922 and 924 is specified.

Usually the request will be for less than all data concerning a Health Data Code. The request can specify a range, such as employees with systolic blood pressure over 160, or can specify an action concerning the health data code, such as operated on for an appendicitis, or other such limitation. A comparator 952 compares each medical data from the main Medical memory with request criteria to select the applicable uses of the health data code.

The medical data meeting the request criteria are held in temporary output storage 744. Report generator 746 reorganizes the data into a designated report format. The reorganization may include a statistical analysis of the data by computer means 748. The statistical analysis may be used, for example, to report the mean pulse rate and standard deviations from the mean for the employee population exposed to a selected hazardous substance. The reports may be displayed or CRT display 12, a report printer, or other display means.

Requests which are not keyed to the employee population or specific medical data, may bypass several host memories. For example, requests not keyed to potentially hazardous substances may bypass memory means 510 and 602 as illustrated by path A'. A request such as the level of a potentially hazardous substance detected by an automatic monitoring station may bypass the host Employee memory 302, main Medical memory 714, and Chemical/Agents memory 510 and Material memory 602 but pass instead through host Location memory 416.

For the employee's well-being and to meet government requirements, certain employees must be examined from time-to-time. For example, employees working in contact with certain hazardous substances must have a medical checkup every six months. Other employees having potentially dangerous diagnosed medical conditions should be examined periodically. Similarly, various criteria necessitate reexaminations with a varying periodicity. To facilitate meeting this need, the Mini-Employee memory means 312 maintains a record of employees due for examinations.

Figure 6:
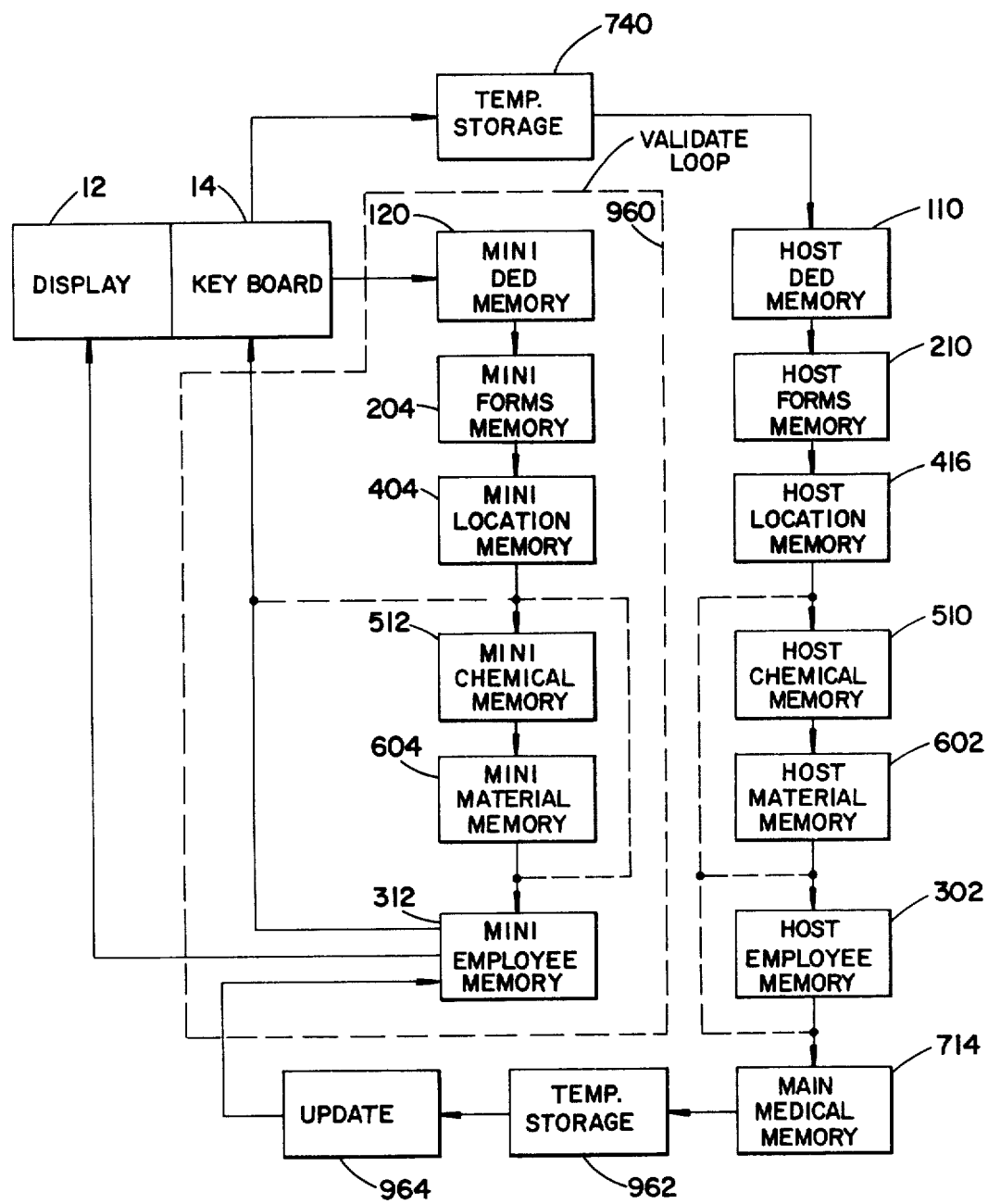
FIG. 6 is illustrative of data flow during appointment generation.

FIG. 6 is illustrative of flow paths for generating examination appointments. The criteria necessitating examination is entered, such as on keyboard 14. The criteria is validated in a validation loop 960. This loop analogous to loop 950 compares encoded parts of the criteria with permissable codes in the appropriate Mini-Memory means.

If all codes are valid, the criteria passes to temporary storage 740. The criteria are channelled to host Data Element Dictionary memory 110, host Forms memory 210 and host Location memory 416. If appropriate to the criteria, they are also channelled to the host Chemical memory 510, the host Material memory 602 or the host Employee memory 302.

As set forth in connection with FIG. 5, these host memories identify the appropriate Health Data Codes, locations within questionnaires, work locations, and the like for the entered criteria. From these identifications the pertinent storage areas of Main Medical memory 714 are caused to be examined and a list of the employees meeting the criteria generated. This list of employees is stored in a temporary storage means 962. An update means 964 updates Mini-Employee memory 312 with the list from temporary storage 962.

The list of employees due for an examination may be displayed in whole or in part in numerous formats.

The above system may be embodied in numerous computer hardware configurations. A preferred configuration is to use a CRT/keyboard terminal, a Datapoint 6600 Minicomputer, and an IBM 370. In this embodiment the Mini-memories, incoming data temporary storage, and means operating directly therefrom may be programmed into the Datapoint 6600. The various sorting and organizing means interface between the Datapoint 6600 and the IBM 370. Such sorting and organizing means may include complimentary interfacing programs in both the Datapoint 6600 and the IBM 370. The seven host memory means, updating means, and means operating directly therefrom may be programmed into the IBM 370. In the preferred embodiment, seven Data Bases are used, one for each of the subsystem means. Other computers may similarly be used.

The exact programs to implement the invention, if one or more programmable computers or minicomputers are used, varies with the computers, data base organization, programming language and like factors chosen for the implementation. Programs which implement the above data flow and logic are preferred.

The invention has been described with reference to the preferred embodiment. Clearly numerous modifications and alterations will occur to others upon reading and understanding this specification. It is our intention to include all such modifications and alterations insofar as they come within the scope of the appended claims or the equivalents thereof.

The invention claimed is:

1. A method of manipulating data concerning the health of a plurality of employees in a computer system, each of the employees working in at least one work location, each of the employees being identifiable by an employee identification and each of the work locations being identifiable by a work location identification, substances of which at least some are potentially hazardous being or having been present in at least one of the work locations, each of the substances being identifiable by a substance identification, the computer system having a substance data base for storing substance identifications, an employee identification data base for storing employee identifications, and an employee health data base for storing employee health data concerning each of the identified employees, said method comprising:

storing in the employee identification data base an identification of each employee and in conjunction with each stored employee identification storing a work location identification for each work location at which the employee has worked and in conjunction with each stored location identification storing an identification of the date the employee has worked at that work location;

updating the employee identification data base with the steps of entering new employee identifications when new employees are hired; entering additional work location identifications and date identifications in conjunction with each stored employee identification when the identified employee changes work locations;

storing in the substance data base substance identifications of substances which are or have been used and in conjunction with each substance identification storing the work location identification of each work location at which the substance has been present and in conjunction with each work location identification an identification of the dates the substance was present at that work location;

updating the substance data base including the steps of: entering additional substance identifications when additional substances are used and entering additional work location identifications and date identifications in conjunction with each stored substance identification when the use of that substance is commensed or discontinued at the identified work location;

storing in the employee health data base the employee identification of each employee and in conjunction with each employee identification, health data concerning the employee identified; and updating the employee health data base including the steps of: entering additional employee identifications of new employees; entering additional health data in conjunction with each stored employee identification as new health data is acquired concerning the identified employee;

whereby data is stored in interrelated data bases for relatively easy retrieval of data concerning employees, substances, work locations, employee health, and combinations thereof.

2. The method as set forth in claim 1 wherein each work location corresponds to a geographical or physical area of a work facility which may be dedicated to a specific manufacturing, process, or operation and wherein the computer system includes a location data base for storing work location identifications and in conjunction with each work location identification an indication of its geographical physical area of the work facility, the method further comprising the steps of:

storing in the location data base each work location identification and in conjunction with each work location identification, an indication of the physical boundaries of the work location and an identification of the date that the work location with the indicated physical boundaries was in use; and updating the location data base by entering new location identifications when new work locations are created by adding additional facilities or by rearranging the physical boundaries of a work location within an existing facility and entering the physical boundaries of each additional work location and identifications of the dates that each work location was in use.

3. The method as set forth in claim 2 wherein means are present in at least one work location for monitoring physical conditions in the work location and wherein the location data base further stores in conjunction with each work location identification data monitored in the work location, the method further comprising:

storing physical condition data in conjunction with the corresponding work location identification.

4. The method as set forth in claim 1 wherein health data is collected on predetermined forms each form of which has a form identification and a predetermined list of health related questions and wherein computer system includes a forms data base for storing the form identifications and the significance of the health related questions on each form, the method further comprising the steps of:

wherein the step of storing health data in the employee health data base comprises storing an identification of one of the predetermined forms and a series of health data corresponding to the answers to the health related questions on the predetermined form without storing the health related questions or the significance of the answers;

storing in the forms data base each forms identification and in conjunction with each forms identification, an identification of the health significance of each health related question on the predetermined form; and updating the forms data base by entering additional form identifications and in conjunction with each form identification the health significance of each health related question on the form, whereby the significance of health data stored in said employee health data base is determinable with reference to the forms data base.

5. The method as set forth in claim 4 wherein the identification of health significance of each health related question is based on the identification number from the International Classification of Diseases, Hospital Adaption.

6. The method as set forth in claim 4 wherein the health related questions are directed to the results of laboratory tests.

7. The method as set forth in claim 1 wherein the step of updating the employee health data base further includes:
 assigning to each of a plurality of at least medical conditions an identifying health code;
 clarifying the health code with clarifier codes for identifying the context in which the health code is used.

8. The method as set forth in claim 7 wherein said health code is the International Classification of Diseases Abstracted, Hospital version.

9. The method as set forth in claim 7 wherein an identifying health code is further assigned to maladies, treatments, medications, accidents and exposure to potentially hazardous substances.

10. The method as set forth in claim 7 wherein the clarifier codes identify, whether the health code represents a laboratory test concerning the medical condition, the laboratory procedure employed and the type of laboratory test.

11. The method as set forth in claim 7 wherein the employee health data base includes a plurality of storage locations which are identified by corresponding storage location identifiers and
 monitoring the clarifier codes and in response to at least one clarifier code generating a series of storage location identifications; and
 storing medical data at the corresponding identified storage locations.

12. The method as set forth in claim 11 wherein the computer system includes a display means for displaying textual messages and further including displaying a textual message in response to at least one clarifier code indicative of the nature of the medical data stored.

13. The method as set forth in claim 11 wherein the computer system includes retrieval means for retrieving medical data from the employee health data base, comparing means for comparing medical data with selected limiting criteria, and display means for displaying medical data and further including
 determining storage location identifications for stored medical data to be retrieved;
 retrieving the stored medical data from the determined storage location;
 comparing the retrieved medical data with limiting criteria; and
 displaying the retrieved medical data meeting the limiting criteria.

14. A method of manipulating data concerning the health of a plurality of employees in a computer system, each of the employees working in at least one work location, each of the employees being identifiable by an employee identification and each of the work locations being identifiable by a work location identification, substances of which at least some are potentially hazardous being or having been present in at least one of the work locations, each of the substances being identifiable by a substance identification, the computer system including a host computer having a substance data base for storing substance identifications, an employee identification data base for storing employee identifications, and an employee health data base for storing employee health data concerning each of the identified employees and mini-computer means having at least a substance memory means, an employee identification memory means and an employee health data memory means, said method comprising the steps of:
 storing in the employee identification data base an identification of each employee and in conjunction with each stored employee identification storing a work location identification for each work location at which the employee has worked and in conjunction with each stored location identification storing an identification of the date the employee has worked at that work location;
 updating the employee identification data base including the steps of entering additional employee identifications, additional work location identifications and additional date identifications into the employee identification memory means of the mini-computer means and transferring the identifications from the mini-computer means to the host computer employee identification data base;
 storing in the substance data base substance identifications of substances which are or have been used and in conjunction with each substance identification, storing the work location identification of each work location at which the substance has been present and, in conjunction with each work location identification, an identification of the dates the substance was present at that work location;
 updating substance data base including the steps of entering additional substance identifications, additional work location identifications, and additional date identifications into the substance memory means of the mini-computer means and transferring the identifications from the mini-computer means to the substance data base of the host computer;
 storing in the employee health data base the employee identification of each employee and in conjunction with each employee identification, health data concerning the employee identified; and
 updating the employee health data base including the steps of entering additional employee identifications and additional health data in the employee health data memory means of the mini-computer means and transferring the employee identifications and the additional health data from the mini-computer means into the employee health data base of the host computer;
 whereby data is stored in interrelated data bases for relatively easy retrieval of data concerning employees, substances, work locations, employee health, and combinations thereof.

15. A method for manipulating in a computer system health data obtained from a plurality of non-predetermined health data forms and predetermined health data forms, each of the predetermined health data forms being adapted to receive a predetermined sequence of solicited health data, the health data being answers to health and medical questions, results of laboratory tests, physicians' findings and diagnoses, and the like, each of the predetermined health data forms being identified by a predetermined health data form code, each of the non-predetermined health data forms being adapted to receive health data and at least one health data code indicative of the significance of the received health data, and wherein the computer system comprises a forms data base for storing the predetermined health data form codes for each of the predetermined health data forms and for storing in conjunction with each of the predetermined health data form codes a sequence of health data codes which is indicative of the significance of health data in the sequence solicited by the predetermined health data form, and an employee health data base for storing an employee identification for each of a plurality of employees and in conjunction with each employee identification, for storing a plurality of predetermined health data form codes and in conjunction with each stored predetermined health data form code storing a plurality of health data, and for storing health data codes and associated health data from non-predetermined data forms, the method comprising:

- entering and storing a plurality of predetermined health data form codes in said forms data base, entering and storing in conjunction with each predetermined health data form code the sequence of corresponding health data codes which indicate the health significance of the sequence of health data solicited by the predetermined health data form;
- updating said forms data base by entering at least one additional predetermined health data form code and associated with the additional predetermined health data form code a corresponding sequence of health data codes;
- storing an employee identification for each employee in the employee health data base;
- conducting an examination of at least one of the identified employees and determining the health data solicited by at least one of the predetermined health data and non-predetermined health data forms;
- entering the employee identification of the examined employee to index the employee health data base, entering and storing in conjucntion with the employee identification in the employee health data base at least one of: (a) a predetermined health data form code which identifies the predetermined data form and entering the health data in the sequence solicited by the predetermined health data form and storing the entered health data without the corresponding health data codes in conjunction with the preselected health data form code in the employee health data base and (b) the health data solicited by the non-predetermined health data form and the corresponding health data codes; and
- indexing the forms data base with a selected health data code to select the predetermined health data form codes and positions within the predetermined health data forms that the health data corresponding to the selected health data code is solicited, retrieving from the employee health data base health data which is stored in conjunction with the selected predetermined health data form codes at the selected positions, and indexing the employee health data base with the selected health data code and retrieving the health data stored in conjunction with the health data code, whereby health data from predetermined and non-predetermined health data forms for the plurality of employees relating to the health condition indicated by the selected health data code is retrieved.

16. A computer system for manipulating health data obtained from at least one of a plurality of predetermined health data forms and non-predetermined health data forms, each of the predetermined health data forms soliciting health data in a predetermined sequence, each of the predetermined health data forms being identified by a predetermined health data form code, each of the non-predetermined health data forms being adapted to receive health data and at least one health data code which indicates the significance of the received health data, the health data being answers to health and medical questions, results of laboratory tests, physicians findings and diagnoses, and the like, the computer system comprising:

- a forms data base for storing the predetermined health data forms codes and for storing in conjunction with each predetermined health data forms code a sequence of health data codes which indicate the significance of the health data solicited by the corresponding predetermined health data forms;
- an employee health data base for storing an employee identification for each of a plurality of employees and for storing in conjunction with each employee identification at least one predetermined health data form code and for storing in conjunction with said at least one predetermined health data form code a sequence of health data in the same order as the forms data base stores the sequence of health data codes in conjunction with said at least one predetermined health data form code such that for predetermined health data forms the health data is stored in the employee health data base and the corresponding health data codes are stored in the forms data base, and, the employee health data base further storing health data solicited by a non-predetermined health data form with corresponding health data codes which indicate the signficance of the solicited health data such that for non-predetermined health data forms the health data and corresponding health data codes are both stored in the employee health data base;
- updating means for updating the forms data base and the employee health data base, the updating means including means for entering additional preselected health data forms codes and a corresponding sequence of health data codes such that additional predetermined health data forms are created and means for entering additional employee identifications such that new employees are added;
- health data entry means for entering health data in the employee health data base, the health data entry means including means for entering a predetermined health data from code and a sequence of health data and means for entering health data and corresponding health data codes; and
- health data retrieving means for retrieving selected health data, the health data retrieving means including means for retrieving from the forms data base predetermined health data form codes and position within the sequence of health data at which the selected health data is stored, means for retrieving from the employee health data base the health data following each retrieved predetermined health data form code at the retrieved sequence position and for retrieving health data stored in conjunction with the health data code corresponding to the selected health data, such that the health data retrieving means retrieves the selected health data for all employees whether stored in the employee health data base in conjunction with predetermined health data form codes or health data codes.

17. A computer system for manipulating data concerning the health of a plurality of employees, each of the employees working in at least one work location, each of the employees being identifiable by an employee identification and each of the work locations being identifiable by a work location identification, substances of which at least some are potentially hazardous being or having been present in at least one of the work locations, each of the substances being identifiable by a substance identification; the computer system comprising:

an employee identification data base means for storing an identification of each employee, a work location identification for each work location at which the employee has worked, and an identification of the date the employee has worked at that work location;

a substance data base means for storing substance identifications of substances which are or have been used, the work location identification of each work location at which each substance has been present, and an identification of the dates each substance was present at each identified work location;

an employee health data base means for storing the employee identification of each employee and health data concerning the employee identified in conjunction with each employee identification; and updating means for updating at least the employee identification data base means, the substance data base means and the employee health data base means, the updating means including means for entering in the employee identification data base means new employee identifications when new employees are hired, means for entering in the employee identification data base means additional work location identifications and data identifications when the identified employee changes work locations, means for entering in the substance data base means additional substance identifications when additional substances are used, means for entering in the substance data base means additional work location identifications and data identifications in conjunction with each stored substance identification when the use of that substance is commensed or discontinued at the identified work location, means for entering in the employee health data base means additional employee identifications of new employees, and means for entering in the employee health data base means additional health data in conjunction with each stored employee identification as new health data is acquired concerning the identified employee;

whereby data is stored in interrelated data bases for relatively easy retrieval of data concerning employees, substances, work locations, employee health, and combinations thereof.

18. The system as set forth in claim 17 further including:

editing means for extracting at least preselected additional health data which is entered by the updating means; and display means for displaying at least the preselected health data extracted by the editing means, whereby reports on preselected medical problems are generated as the data bases are updated.

19. The system as set forth in claim 17 further including:

retrieval means for retrieving requested data from the employee identification data base means, the substance data base means, and the employee health data base means;

a report generator for reorganizing the requested data retrieved by the retrieval means into a preselected report format; and display means for displaying the requested data in the preselected report format, whereby preselected reports are retrieved from the data base means.

20. The system as set forth in claim 17 wherein each work location corresponds to a geographical or physical area of a work facility is and wherein the computer system includes a location data base means for storing work location identifications and in conjunction with each work location identification an indication of its physical area in the work facility and an indication of the date that the work location with the indicated physical area was in use.

21. The system as set forth in claim 17 wherein health data is collected on predetermined forms each form of which has a form identification and a predetermined list of health related questions and wherein computer system includes a forms data base means for storing the form identifications and the significance of the health related questions on each form.

22. The computer system as set forth in claim 17 wherein the health data includes: a four byte health code from the International Classification of Diseases Abstracted, hospital version for identifying a medical condition; a plurality of clarifier bytes for identifying the context in which the health code is used, and wherein the employee health data base means includes means for storing the four byte health code and the clarifier bytes.

23. The computer system as set forth in claim 22 wherein the clarifier bytes identify whether the health code represents a diagnosis of the medical condition, the source of diagnosis, and the time of existence of the medical condition.

24. The computer system as set forth in claim 23 wherein the clarifier code includes prefix and suffix clarifiers.

25. The computer system as set forth in claim 23 wherein the clarifier codes identify at least the source and time of existence of the medical condition.

26. The computer system as set forth in claim 22 wherein the clarifier bytes identify whether the health data code represents a laboratory test concerning the medical condition, and the type of laboratory test.

* * * * *

UNITED STATES PATENT AND TRADEMARK OFFICE
CERTIFICATE OF CORRECTION

PATENT NO. : 4,347,568
DATED : August 31, 1982
INVENTOR(S) : Giguere et al.

It is certified that error appears in the above—identified patent and that said Letters Patent is hereby corrected as shown below:

In column 2, line 1 delete "an" and insert -- and --.
In column 2, line 1 delete "unertaken" and insert -- undertaken --.
In column 3, line 60 delete "sybsystem" and insert -- subsystem --.
In column 4, line 3 delete "an" and insert -- and --.
In column 4, line 57 delete "an" and insert -- a --.
In column 5, line 6 delete "textural" and insert -- textual --.
In column 5, line 11 delete "textural" and insert -- textual --.
In column 9, line 7 delete "concantenating" and insert -- concatenating --.
In column 10, line 16 delete "otherhand" and insert -- other hand --.
In column 11, line 31 delete "or" and insert -- of --.
In column 13, line 57 delete "laboaratory" and insert -- laboratory --.
In column 14, line 47 delete "determintion" and insert -- determination --.

UNITED STATES PATENT AND TRADEMARK OFFICE
CERTIFICATE OF CORRECTION

PATENT NO. : 4,347,568

DATED : August 31, 1982

INVENTOR(S) : Giguere et al.

Page 2 of 2

It is certified that error appears in the above—identified patent and that said Letters Patent is hereby corrected as shown below:

In column 21, line 52 after "including" insert -- : --.

Signed and Sealed this

Twenty-second Day of March 1983

[SEAL]

Attest:

GERALD J. MOSSINGHOFF

*Attesting Officer*     *Commissioner of Patents and Trademarks*